US012653644B2

(12) United States Patent
Mayfield et al.

(10) Patent No.: US 12,653,644 B2
(45) Date of Patent: Jun. 16, 2026

(54) IMPLANT WITH HIGH PRIMARY STABILITY AND ACCELERATED SECONDARY STABILITY

(71) Applicant: Biomet 3i, LLC, Palm Beach Gardens, FL (US)

(72) Inventors: Robert L. Mayfield, Jupiter, FL (US); Michael D. Scalise, West Palm Beach, FL (US); Zachary B. Suttin, West Palm Beach, FL (US)

(73) Assignee: BIOMET 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 18/233,643

(22) Filed: Aug. 14, 2023

(65) Prior Publication Data

US 2023/0398657 A1 Dec. 14, 2023

Related U.S. Application Data

(63) Continuation of application No. 16/503,762, filed on Jul. 5, 2019, now abandoned, which is a continuation
(Continued)

(51) Int. Cl.
*A61C 8/00* (2006.01)
*A61C 13/00* (2006.01)

(52) U.S. Cl.
CPC .......... *A61C 8/0012* (2013.01); *A61C 8/0039* (2013.01); *A61C 8/0024* (2013.01);
(Continued)

(58) Field of Classification Search
CPC ... A61C 8/0012; A61C 8/0013; A61C 8/0015; A61C 2008/0046
See application file for complete search history.

(56) References Cited

U.S. PATENT DOCUMENTS 5,338,197 A * 8/1994 Kwan ................. A61C 8/0022
433/174
5,360,448 A 11/1994 Thramann
(Continued)

FOREIGN PATENT DOCUMENTS

CN 201223459 Y 4/2009
CN 101773413 A 7/2010
(Continued)

OTHER PUBLICATIONS

Machine Translation of JP2012137131 (Year: 2012).*
(Continued)

*Primary Examiner* — Edward Moran
(74) *Attorney, Agent, or Firm* — Sheridan Ross P.C.

(57) ABSTRACT

An implant for implantation into bone tissue includes an elongated body having an outer surface. The outer surface has at least one thread. The thread makes a number of turns around the body of the implant and includes a root, a flank and a crest. The root and a segment of the flank have a roughened portion compared to the crest. A method of forming an implant having a threaded outer surface including a root, a flank, and a crest includes treating the threaded outer surface at only the root and a portion of the flank while the crest remains untreated.

16 Claims, 5 Drawing Sheets

Related U.S. Application Data of application No. 14/682,826, filed on Apr. 9, 2015, now Pat. No. 10,414,022.

(60) Provisional application No. 61/978,731, filed on Apr. 11, 2014.

(52) U.S. Cl.
CPC .. *A61C 2008/0046* (2013.01); *A61C 13/0007* (2013.01); *A61F 2250/0025* (2013.01)

(56) References Cited

U.S. PATENT DOCUMENTS

| | | | |
|---|---|---|---|
| 5,571,017 A | 11/1996 | Niznick | |
| 5,727,943 A | 3/1998 | Beaty | |
| 5,829,978 A * | 11/1998 | Day | A61C 8/0012 |
| | | | 433/173 |
| 5,863,201 A | 1/1999 | Lazzara | |
| 5,871,356 A | 2/1999 | Guedj | |
| 5,876,453 A | 3/1999 | Beaty | |
| 5,885,079 A | 3/1999 | Niznick | |
| 5,902,109 A | 5/1999 | Reams, III et al. | |
| 5,989,027 A | 11/1999 | Wagner | |
| 6,048,204 A | 4/2000 | Klardie | |
| 6,090,999 A | 7/2000 | Bruce | |
| 6,095,817 A * | 8/2000 | Wagner | A61C 8/0012 |
| | | | 433/173 |
| 6,102,703 A | 8/2000 | Day | |
| 6,117,249 A | 9/2000 | Erikson | |
| 6,287,117 B1 | 9/2001 | Niznick | |
| 6,379,153 B1 | 4/2002 | Schroering | |
| 6,379,154 B2 | 4/2002 | DeVincenzo | |
| 6,386,876 B1 | 5/2002 | Lee | |
| 6,402,516 B2 | 6/2002 | Ihde | |
| 6,419,492 B1 | 7/2002 | Schroering | |
| 6,431,869 B1 | 8/2002 | Reams, III | |
| 6,491,723 B1 | 12/2002 | Beaty | |
| 6,547,564 B1 | 4/2003 | Hansson | |
| 6,599,322 B1 | 7/2003 | Amrich | |
| 6,620,332 B2 | 9/2003 | Amrich | |
| 6,626,671 B2 | 9/2003 | Klardie | |
| 6,652,765 B1 | 11/2003 | Beaty | |
| 6,969,474 B2 | 11/2005 | Beaty | |
| 6,991,463 B2 | 1/2006 | Ihde | |
| 7,018,418 B2 | 3/2006 | Amrich | |
| 7,048,541 B2 | 5/2006 | Hall | |
| 7,125,253 B2 | 10/2006 | Kitamura | |
| 7,169,317 B2 | 1/2007 | Beaty | |
| 7,238,186 B2 | 7/2007 | Zdeblick | |
| 7,250,055 B1 | 7/2007 | Vanderwalle | |
| 7,258,810 B2 | 8/2007 | Hunter | |
| 7,264,470 B2 | 9/2007 | Hansson | |
| 7,338,493 B1 | 3/2008 | Vandewalle | |
| 7,341,453 B2 | 3/2008 | Coatoam | |
| D583,057 S | 12/2008 | Kojima | |
| 7,517,218 B2 | 4/2009 | Hansson | |
| 7,547,399 B2 | 6/2009 | Beaty | |
| 7,550,091 B2 | 6/2009 | Beaty | |
| D595,850 S | 7/2009 | Koch | |
| 7,597,557 B2 | 10/2009 | Fromovich | |
| 7,699,613 B2 | 4/2010 | Niznick | |
| 7,806,693 B2 | 10/2010 | Hurson | |
| 7,845,945 B2 | 12/2010 | Canter | |
| 7,850,862 B2 | 12/2010 | Amrich | |
| 7,857,987 B2 | 12/2010 | Beaty | |
| 7,883,336 B2 | 2/2011 | Hansson | |
| 7,959,440 B2 | 6/2011 | Hansson | |
| 8,029,283 B2 | 10/2011 | Schwarz | |
| 8,029,285 B2 | 10/2011 | Holmen | |
| 8,038,442 B2 | 10/2011 | Hurson | |
| 8,128,402 B2 | 3/2012 | Lundgren | |
| 8,197,255 B2 | 6/2012 | Fromovich | |
| 8,221,119 B1 | 7/2012 | Valen | |
| 8,221,499 B2 | 7/2012 | Lazzara | |

| | | | |
|---|---|---|---|
| 8,221,639 B2 | 7/2012 | Towse | |
| 8,241,036 B2 | 8/2012 | Breitenstein | |
| 8,251,700 B2 | 8/2012 | Robb | |
| 8,277,219 B2 | 10/2012 | Hansson | |
| 8,309,162 B2 | 11/2012 | Charlton | |
| 8,333,590 B2 | 12/2012 | Hansson | |
| 8,337,205 B2 | 12/2012 | Reed | |
| 8,361,381 B2 | 1/2013 | Heuer | |
| 8,382,477 B2 | 2/2013 | Philibin | |
| 8,403,991 B2 | 3/2013 | Ullrich, Jr. | |
| 8,435,302 B2 | 5/2013 | Ullrich, Jr. | |
| 8,439,919 B2 | 5/2013 | Hall | |
| 8,469,710 B2 | 6/2013 | Bondar | |
| 8,480,749 B2 | 7/2013 | Ullrich, Jr. | |
| 8,496,710 B2 | 7/2013 | Bagga | |
| 8,500,449 B2 | 8/2013 | Kwan | |
| 8,545,568 B2 | 10/2013 | Ullrich, Jr. | |
| 8,551,176 B2 | 10/2013 | Ullrich, Jr. | |
| 8,556,987 B2 | 10/2013 | Hunter | |
| 8,562,684 B2 | 10/2013 | Ullrich, Jr. | |
| 8,562,685 B2 | 10/2013 | Ullrich, Jr. | |
| 8,585,765 B2 | 11/2013 | Ullrich, Jr. | |
| 8,585,766 B2 | 11/2013 | Ullrich, Jr. | |
| 8,585,767 B2 | 11/2013 | Ullrich, Jr. | |
| 8,591,590 B2 | 11/2013 | Ullrich, Jr. | |
| 8,617,248 B2 | 12/2013 | Ullrich, Jr. | |
| 8,641,418 B2 | 2/2014 | Mayfield | |
| 8,651,863 B2 | 2/2014 | Schroering | |
| 8,702,806 B2 | 4/2014 | Balay | |
| 8,714,977 B2 | 5/2014 | Fromovich | |
| 8,758,442 B2 | 6/2014 | Ullrich, Jr. | |
| 8,758,443 B2 | 6/2014 | Ullrich, Jr. | |
| 8,764,443 B2 | 7/2014 | Hall | |
| 8,814,939 B2 | 8/2014 | Ullrich, Jr. | |
| 8,827,703 B2 | 9/2014 | Hall | |
| 8,834,571 B2 | 9/2014 | Bagga | |
| 8,940,053 B2 | 1/2015 | Ullrich, Jr. | |
| 8,992,619 B2 | 3/2015 | Patterson | |
| 8,992,622 B2 | 3/2015 | Ullrich, Jr. | |
| 9,011,546 B2 | 4/2015 | Ullrich, Jr. | |
| 10,414,022 B2 | 9/2019 | Mayfield et al. | |
| 2002/0061494 A1* | 5/2002 | Klardie | A61C 8/0012 |
| | | | 433/174 |
| 2003/0158554 A1 | 8/2003 | Hall | |
| 2005/0147942 A1 | 7/2005 | Hall | |
| 2006/0204930 A1 | 9/2006 | Sul | |
| 2010/0159418 A1* | 6/2010 | Hall | A61C 8/0022 |
| | | | 433/201.1 |
| 2011/0306016 A1 | 12/2011 | Hansson | |
| 2013/0248487 A1 | 9/2013 | Mayfield | |
| 2019/0329378 A1 | 10/2019 | Mayfield et al. | |
| 2022/0087784 A1 | 3/2022 | Gilgenbach Blume et al. | |

FOREIGN PATENT DOCUMENTS

| | | | |
|---|---|---|---|
| CN | 103252728 A | | 8/2013 |
| CN | 106535860 A | | 3/2017 |
| EP | 0794745 | | 6/1996 |
| FR | 2610512 | | 8/1988 |
| JP | H06304186 A | | 11/1994 |
| JP | 2012137131 | * | 7/2012 |
| JP | 2012137131 A | | 7/2012 |
| WO | WO 96/16611 | | 6/1996 |
| WO | WO 01/74412 | | 10/2001 |
| WO | WO 2004/098442 | | 11/2004 |

OTHER PUBLICATIONS

"International Application Serial No. PCT/US2015/025057, International Preliminary Report on Patentability mailed Oct. 20, 2016", 8 pages.

"International Application Serial No. PCT/US2015/025057, International Search Report mailed Aug. 25, 2015", 4 pages.

"International Application Serial No. PCT/US2015/025057, Written Opinion mailed Aug. 25, 2015", 6 pages.

"Chinese Application Serial No. 201580029763.1, Office Action mailed Mar. 13, 2019", (W/ English Translation), 14 pages.

(56) References Cited

OTHER PUBLICATIONS

"European Application Serial No. 15776219.6, Extended European Search Report mailed Oct. 25, 2017", 6 pages.

"European Application Serial No. 19218309.3, Extended European Search Report mailed Dec. 8, 2020", 8 pages.

"U.S. Appl. No. 14/682,826, Advisory Action mailed Apr. 3, 2017", 3 pages.

"U.S. Appl. No. 14/682,826, Appeal Brief filed Aug. 31, 2017", 21 pages.

"U.S. Appl. No. 14/682,826, Appeal Decision mailed Mar. 28, 2019", 8 pages.

"U.S. Appl. No. 14/682,826, Decision on Pre-Appeal Brief mailed Aug. 1, 2017", 1 page.

"U.S. Appl. No. 14/682,826, Examiner's Answer mailed Nov. 14, 2017", 7 pages.

"U.S. Appl. No. 14/682,826, Final Office Action mailed Jan. 18, 2017", 8 pages.

"U.S. Appl. No. 14/682,826, Non Final Office Action mailed Aug. 11, 2016", 9 pages.

"U.S. Appl. No. 14/682,826, Notice of Allowance mailed Apr. 8, 2019", 7 pages.

"U.S. Appl. No. 14/682,826, Pre-Appeal Brief Request filed Jun. 19, 2017", 5 pages.

"U.S. Appl. No. 14/682,826, Reply Brieffiled Jan. 15, 2018", 7 pages.

"U.S. Appl. No. 14/682,826, Response filed Mar. 20, 2017 to Final Office Action mailed Jan. 18, 2017", 12 pages.

"U.S. Appl. No. 14/682,826, Response filed Nov. 11, 2016 to Non Final Office Action mailed Aug. 11, 2016", 12 pages.

Official Action for U.S. Appl. No. 16/503,762, dated May 27, 2021 9 pages, Restriction Requirement.

Official Action for U.S. Appl. No. 16/503,762, dated May 27, 2021 15 pages.

Final Action for U.S. Appl. No. 16/503,762, dated Dec. 24, 2021 12 pages.

Official Action for U.S. Appl. No. 16/503,762, dated Jul. 5, 2022 14 pages.

Final Action for U.S. Appl. No. 16/503,762, dated Dec. 12, 2022 13 pages.

Official Action for U.S. Appl. No. 16/503,762, dated Mar. 14, 2023 14 pages.

* cited by examiner

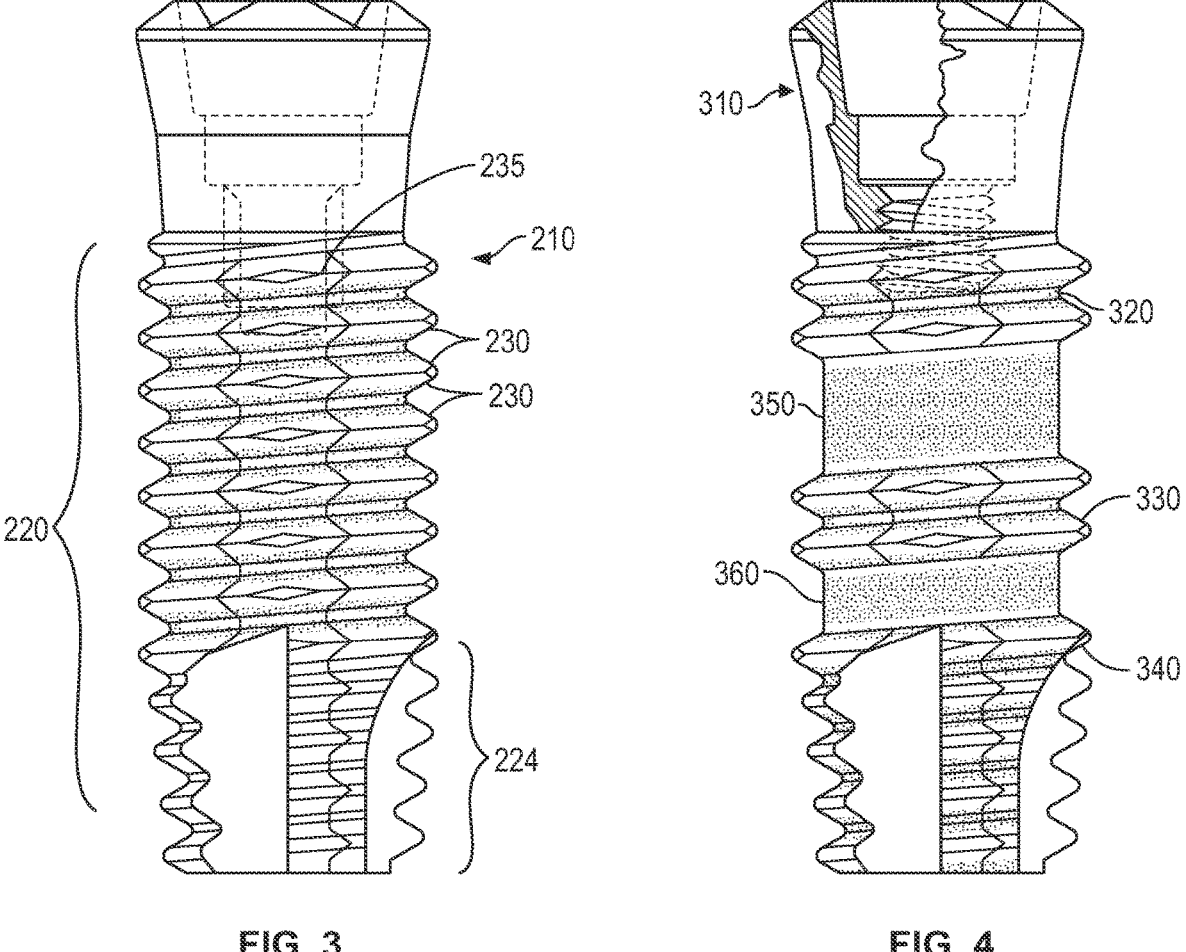
FIG. 3                    FIG. 4

| |
|---|
| Provide Implant Having Threaded Outer Surface |

700

| |
|---|
| Treat Outer Surface Of Implant Such That Root And Portion Of Flank Are Roughened |

701

| |
|---|
| Treat Crest, Flank and Root |

702

IMPLANT WITH HIGH PRIMARY STABILITY AND ACCELERATED SECONDARY STABILITY

CROSS-REFERENCE TO RELATED APPLICATIONS

This application is a continuation of U.S. patent application Ser. No. 16/503,762, filed on Jul. 5, 2019, which is a continuation of U.S. patent application Ser. No. 14/682,826, filed on Apr. 9, 2015, now U.S. Pat. No. 10,414,022 issued on Sep. 17, 2019, which claims priority to and the benefits of U.S. Provisional Application No. 61/978,731, filed Apr. 11, 2014, all of which are incorporated herein by reference in their entireties.

COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE PRESENT DISCLOSURE

The present disclosure relates to improvements in screw-type dental implants and, in particular, to dental implants having a roughened surface topography and methods of making the same.

BACKGROUND

It is becoming more common to replace a missing tooth with a prosthetic tooth that is placed upon and attached to a dental implant. Dental implants are often comprised of metal and metal alloys, including titanium (Ti) and titanium alloys. The dental implant serves as an artificial root that integrates with the gingiva and the bone tissue of the mouth.

For the dental implant to function successfully, sufficient osseointegration is required. In other words, a bond between the implant and the bone must be formed and retained. The surface of the implant may be roughened to help enhance the osseointegration process. Non-limiting examples of processes for roughening an implant surface include acid etching, grit blasting, or a combination thereof, which impart roughness on the surface.

Roughening the surface of an implant, however, can lead to a compromise in the integrity of the implant's cutting geometry. More specifically, roughening the crests of the implant's thread can lead to rolling the edge of the crests and/or eroding the peaks of the crests. Additionally, roughening of the crests can change the machined macrogeometry (or thread features) intended to initially stabilize the implant. Robust initial stability is a requirement for long-term stability (permanent fixation of the implant), and without it, the implant can be more susceptible to non integration or even loss of integration, both of which generally require implant retrieval. Furthermore, the change in macrogeometry can alter the tactile feedback felt by a clinician during implant placement. This is critical, as the "feel" of the implant during installation can serve as a directional indicator by which additional clinical decisions are made (e.g., restore the implant immediately, delay loading of the implant, remove the implant, place additional torque on the implant postseating, etc.). Unfortunately, a change in tactile feedback, such as what could result from small changes in macrogeometry, can create a false positive or false negative, and can leave the clinician misinformed.

SUMMARY

An implant for implantation into bone tissue includes an elongated body. The elongated body has an upper portion configured to receive a prosthesis and a lower portion for being submerged in the bone tissue. The elongated body of the implant also includes an outer surface. The implant also includes at least one thread on the outer surface of the body. The thread makes a number of turns around the body between the upper and lower portions and includes a root, a flank, and a crest. The root and a segment of the flank have a roughened portion compared to the crest.

In another aspect of the invention, another implant for implantation into bone tissue includes at least one thread. The thread makes a number of turns around the implant. The implant also includes a roughened portion adjacent to a root of the thread, and the roughened portion extends along a length of the implant while a crest of the thread remains relatively smooth.

In a further aspect of the invention, a method of forming an implant having a threaded outer surface including a root, a flank, and a crest includes treating the threaded outer surface. More specifically, the method includes treating the threaded outer surface at only the root and a portion of the flank while the crest remains untreated.

Additional aspects of the present disclosure will be apparent to those of ordinary skill in the art in view of the detailed description of various aspects, which is made with reference to the drawings, a brief description of which is provided below.

BRIEF DESCRIPTION OF THE DRAWINGS

FIG. 3 illustrates a side view of an implant according to a third implementation of the present invention;

FIG. 4 illustrates a side view of an implant according to a fourth implementation of the present invention;

DETAILED DESCRIPTION

Figures 1, 2:
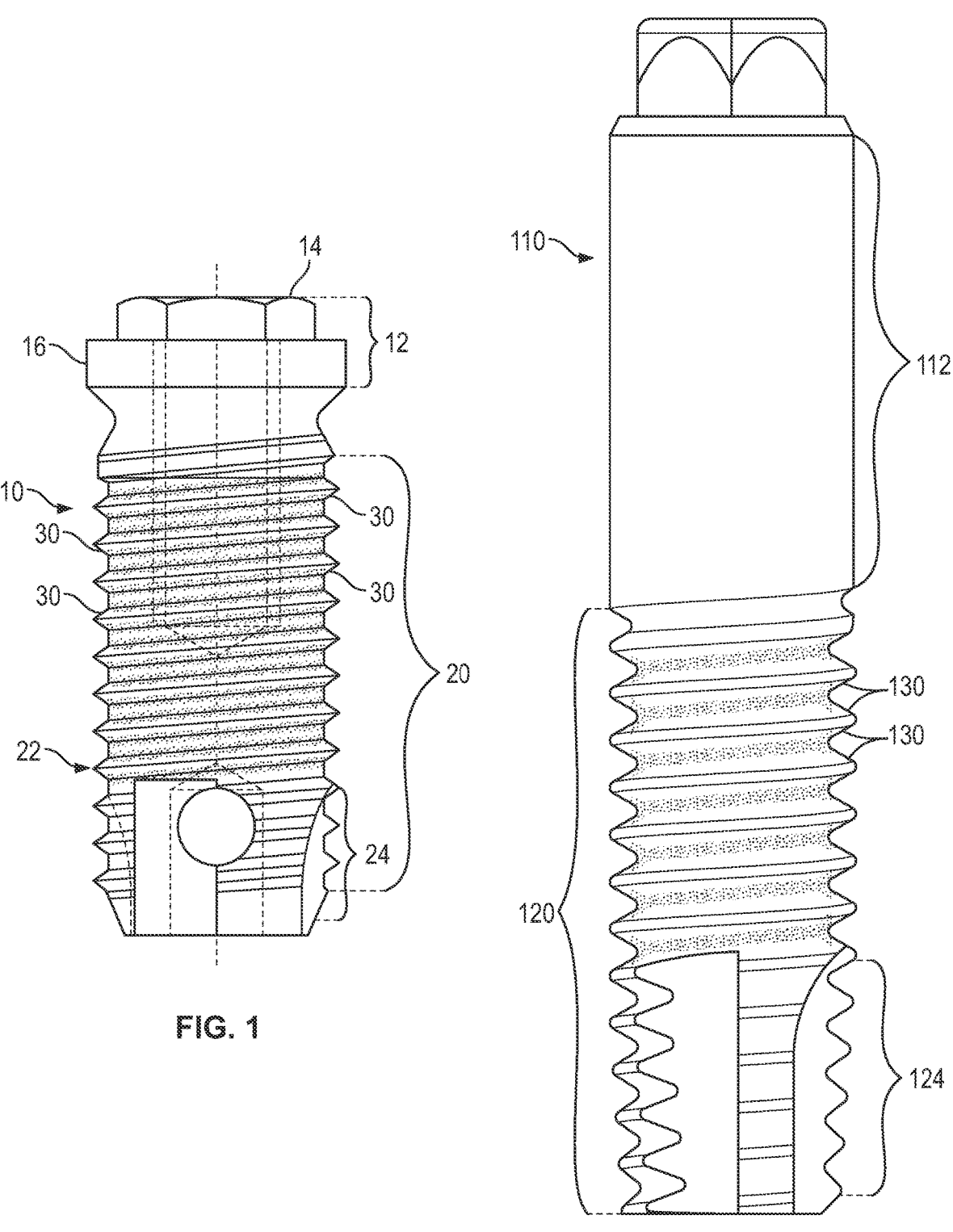
FIG. 1 illustrates a side view of an implant according to a first implementation of the present invention.
FIG. 2 illustrates a side view of an implant according to a second implementation of the present invention.

While the present disclosure can be embodied in many different forms, there is shown in the drawings and will be described various exemplary aspects of the present disclosure with the understanding that the present disclosure is to be considered as an exemplification of the principles thereof and is not intended to limit the broad aspect of the present disclosure to the illustrated aspects.

FIG. 1 illustrates a side view of an implant 10 according to a first implementation. The implant 10 may, for example, be made of titanium or alloys thereof. FIGS. 2, 3, 4, and 5 which are discussed below, describe alternative implant designs that may also be used according to certain implementations of the disclosed subject matter.

The implant 10 has an elongated body. The top of the elongated body includes a head portion 12, which includes a non-rotational boss 14. In the illustrated implementation of FIG. 1, the boss 14 is hexagonal. The boss 14 is configured to be engageable with a tool that screws the implant 10 into bone tissue. The boss 14 is also used for non-rotationally engaging a correspondingly-shaped socket on a restorative or prosthetic component (e.g., an abutment with a tooth-shaped crown attached thereto) that is attached to the implant 10. The head portion 12 also includes a collar 16.

A threaded bottom portion 20 facilitates bonding with bone or gingiva. The threaded bottom portion 20 includes a thread 22 that makes a plurality of turns around the implant 10. The turns are typically in a helical pattern, as shown in FIG. 1 In certain implementations, the threaded bottom portion 20 may include multiple threads, so as to define a multi-lead thread.

Further, each of the turns of the thread 22 includes a root region, a flank region and a crest region. The root region of a turn in the thread 22 is located at a minor diameter with respect to a central axis of the implant 10, while the crest region is located at a major diameter with respect to the central axis of the implant 10. The flank region is the surface connecting the root and the crest regions. The crest region provides primary stability for the implant 10 by ensuring a secure mechanical connection between the implant 10 and the bone or gingiva. Different implementations of the root, flank and crest regions will be described in detail with respect to FIGS. 7A-7C and 8A-8C The threaded bottom portion 20 may further include a self-tapping region 24 with incremental cutting edges that allows the implant 10 to be installed without the need for a bone tap.

The thread 22 includes a roughened portion 30. The roughened portion 30 can aid in the osseointegration process by improving the integration between bone or gingiva and the implant 10. This improved integration provides a secondary level of stability for the implant. The roughened portion 30 may be generated using a variety of techniques including, for example, acid etching, grit blasting, or a combination thereof. As described below, the preferred roughening technique is grit blasting. As illustrated in FIG. 1, the roughened portion 30 is located on the root and flank regions of the thread 22, but not on the crest regions. A transition region from the roughened portion to the relatively smoother surface occurs along the thread's flank regions between the root and crest regions. In certain implementations, the transition region includes a portion of varying roughness in the direction of the crest. For example, in the implementation of FIG. 1, the transition region includes a portion of decreasing roughness in the direction of the crest. That is, the transition region decreases in roughness as it approaches the relatively smooth crest. Additionally, as shown in FIG. 1, the self-tapping region 24 of the implant 10 is relatively smooth compared to the roughened portion 30.

A transition point between the roughened portion 30 and the relatively smooth surface of the crest can be chosen to minimize interference with the surface of the crest regions while maximizing osseointegration with the roughened portions on the root and flank regions. As will be described in further detail below with respect to FIGS. 7A-7C and 8A-8C, different transition points can be chosen for different thread geometries.

FIG. 2 illustrates an implant 110 that differs in physical features from the implant 10 of FIG. 1 to allow it to extend through the gingiva. Like the threads of the implant 10, the threads of the implant 110 are in a helical pattern. The implant 110 also includes an elongated middle section 112 that is relatively smooth compared to the roughened portion 130. Similar to the self-tapping region 24 of FIG. 1, the self-tapping region 124 illustrated in FIG. 2 is also relatively smooth compared to the roughened portion 130. The implant 110 also differs from the implant 10 in the details of the roughened portion 130. More specifically, the roughened portion 130 extends up a smaller portion of the flank regions of the implant 110 compared to the roughened portion 30 of the implant 10 of FIG. 1. As described above with respect to FIG. 1, the transition point between the roughened portion and the relatively smooth surface of the implant 110 can be chosen to minimize interference with the cutting surface of the crest regions while maximizing osseointegration with the roughened surfaces on the root and flank regions.

FIG. 3 illustrates a more typical trans-gingival implant 210 that differs from the implant 10 of FIG. 1 and the implant 110 of FIG. 2 in the details of the contours of the threads defining the exterior of the threaded bottom portion 220. Like the implant 10 of FIG. 1 and the implant 110 of FIG. 2, the implant 210 has a roughened portion 230 which is located on the root regions and portions of the flank regions of the implant 210. Additionally, the threads of the implant 210 are also in a helical pattern. The threads of the implant 210 have portions 235 of their crests truncated, as described in U.S. Pat. No. 5,902,109, which is hereby incorporated by reference in its entirety.

FIG. 4 illustrates an implant 310 that includes two thread-less regions 350, 360 interspersed between multiple threaded regions 320, 330, 340. The threaded regions 320, 330, 340 include threads in a helical pattern and are similar to the threaded regions, 20, 120, 220 described above with respect to FIGS. 1-3 in that the threaded regions 320, 330, 340 include roughened surfaces located on their root regions and portions of their flank regions.

As shown in FIG. 4, the threadless regions 350, 360 also include roughened surfaces. As discussed above with respect to FIG. 1, the roughened surfaces provide the implant 310 with a secondary level of stability to help secure the implant after installation. Because the threadless regions 350, 360 lack threads with crests, the entirety of the threadless regions 350,360 can be roughened without requiring a relatively smoother crest area, as required by the implants of FIGS. 1-3. Further, although the implants of FIGS. 1-3 have smooth self-tapping regions, in certain implementations, the root and flank regions of threads in the self-tapping region may be roughened to further increase implant stability, as shown in FIG. 4. As shown in FIG. 4, the crests of these threaded portions in the self-tapping region remain smooth.

Figures 5, 6:
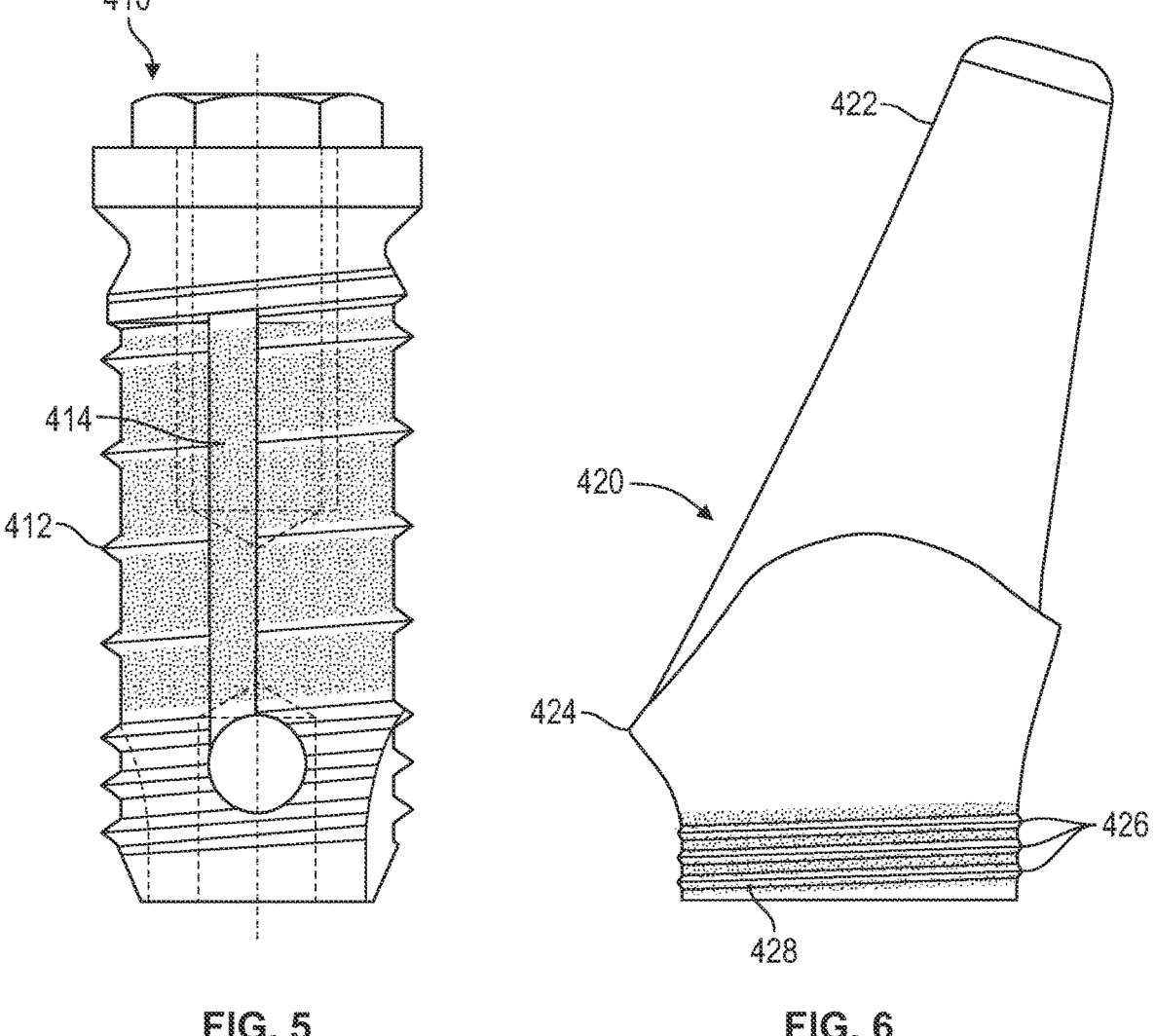
FIG. 5 illustrates a side view of an implant according to a fifth implementation of the present invention.
FIG. 6 illustrates a side view of an abutment that is to be attached to a dental implant, such as the ones in 1-5, according to yet another implementation of the present invention.

FIG. 5 illustrates a trans-gingival implant 410 that differs from the implant 10 of FIG. 1 in the details of the configuration of the thread 412 along the exterior of the threaded bottom portion and in the inclusion of a vertical groove 414 extending up the length of the implant 410. More specifically, the thread 412 has a larger lead compared to the leads illustrated in FIGS. 1-4, which effectively increases the size of the root regions relative to the crest regions of the thread 412. Because the root regions of the thread 412 are larger, the implant 410 has more of its surface roughened compared to the implants shown in FIGS. 1-4. Additionally, as mentioned above, the implant 410 has an extended vertical groove 414 compared to the implants of FIGS. 1-4. The vertical groove 414 is roughened and further improves osseointegration to the implant 410.

FIG. 6 illustrates an abutment 420 configured to attach to both an implant (e.g., one of the implants illustrated in FIGS. 1-5) and to receive a tooth-shaped crown (not shown). The abutment 420 includes an upper portion 422 shaped to receive and securely attach to a dental crown that is typically porcelain. In other implementations, other shapes may be used for the upper portion. The abutment 420 also includes a lower portion 424, which attaches to an implant through an internal socket (not shown) that would be non-rotationally coupled to an external anti-rotational feature of the implant, such as the hexagonal boss 14 on the implant 10 of FIG. L A screw extends through the abutment 420 and engages the internal threads within the bore of the implant to axially secure the abutment 420 on the implant, as is well known in the art. The abutment 420 also includes threads 426 on the lower portion 424, which are similar to the threaded portions of the implants described above with respect to FIGS. 1-5. Specifically, the threads 426 on the abutment 420 include roughened surfaces 428 in the root and flank regions of the threads 426, while the crest regions of the threads 426 remain relatively smooth. As illustrated in FIG. 6, the threads 426 on the abutment 420 are significantly smaller than the threads on the implants described above with respect to FIGS. 1-5. The threads 426 and the roughened surfaces 428 help to promote gingival tissue attachment o the surface of the abutment 420.

As described above, implants according to the disclosed subject matter include at least one thread with portions of varying roughness. The thread can include one or more turns around the central axis of the implants, and each turn can include a root region, a flank region and a crest region. The root region of a turn in thread is located at a minor diameter with respect to the central axis of the implant while the crest region is located at a major diameter with respect to the central axis. The flank region serves as a transition region between the root and the crest regions. As shown in FIGS. 7A-7C and FIGS. 8A-8C, in different implementations, the root, flank and crest regions can have different shapes and can extend at different angles with respect to each other.

Figures 7A, 7B, 7C:
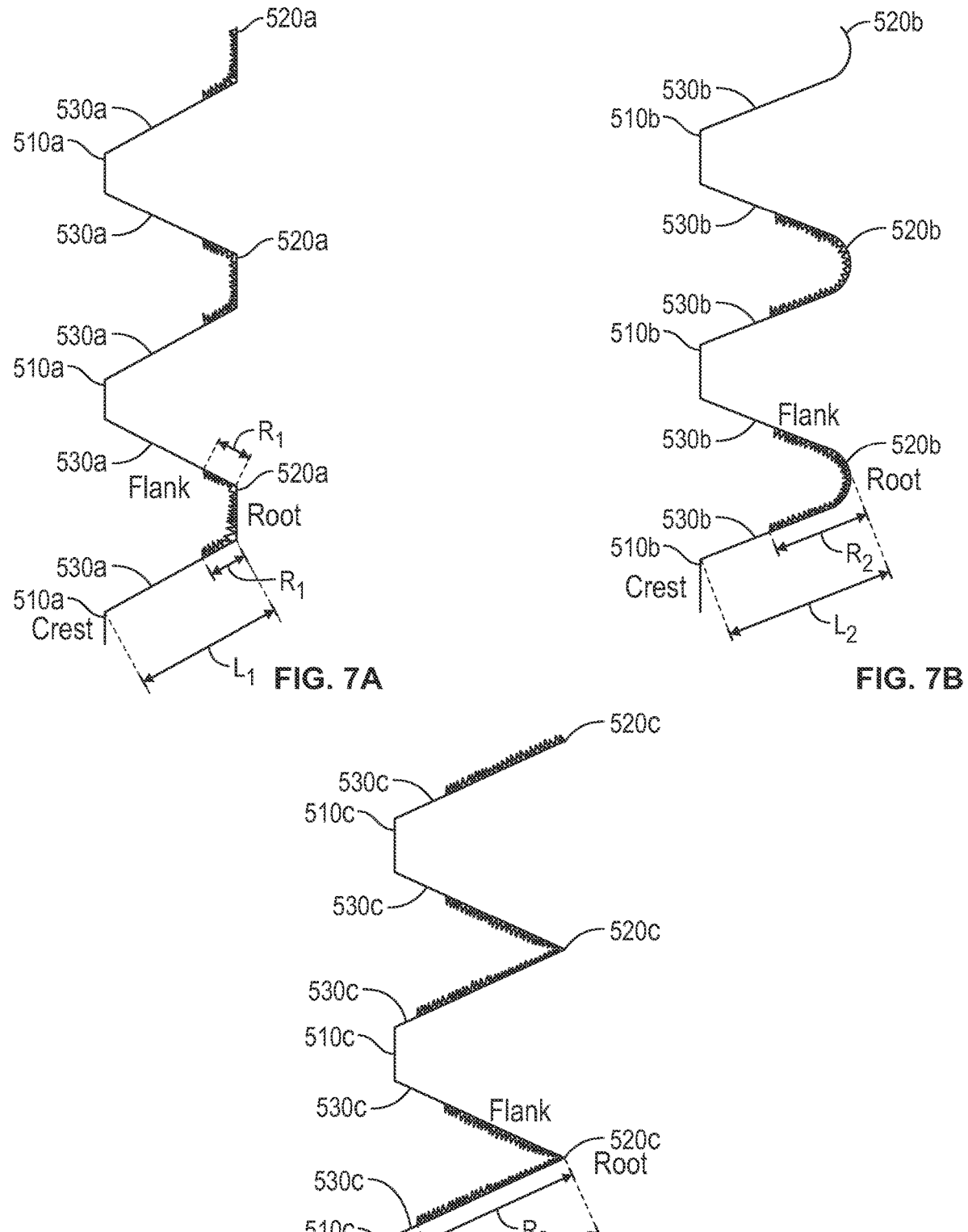
FIG. 7A illustrates a side view of the threaded portion of an implant with a flattened root according to another aspect of the present invention.
FIG. 7B illustrates a side view of the threaded portion of an implant with a rounded root according to another aspect of the present invention.
FIG. 7C illustrates a side view of the threaded portion of an implant with a narrower angled root according to another aspect of the present invention.

FIGS. 7A-7C illustrate side views of the threaded portion of various implants with differently shaped roots according to the disclosed subject matter. Each of the threaded implant portions illustrated in FIGS. 7A-7C includes at least one root, flank, and crest. The threaded portion of FIG. 7A includes crests 510a and roots 520a, each with a flattened shape, and multiple flanks 530a connecting the crests 510a and roots 520a. Each of the flanks 530a has a length 'L$_1$', and a segment of each flank 530a, each segment with a length 'R$_1$', has a roughened portion. The length of the roughened segment, R$_1$, can be chosen based on performance requirements and the geometry of a particular implant For example, the length R$_1$ may be chosen to achieve an acceptable balance between the increased stability offered by the roughened portion and the increase in insertion torque required to install the implant. As shown in FIG. 7A, the roughened portion is on an inner section of each of the flanks 530a relative to a central axis of the implant (central axis not shown). Further, an outer section of each of the flanks 530a (relative to the central axis) has a surface similar to the crests 510a, which is smoother relative to the roughened portion.

In certain implementations, the threaded portions of FIG. 7A include transition regions from the roughened portion to the relatively smoother portions of the flanks 530a and crests 510a. The transition region can optionally include a portion of varying roughness in the direction of the crest 510a. In other implementations, the entire roughened portion can have a similar roughness.

The threaded portion of FIG. 7B is similar to the threaded portion illustrated in FIG. 7A, but includes curved roots 520b instead of flattened roots. Further, each of the flanks 530b has a length 'L$_2$', and a segment of each flank 530b has a roughened portion of length 'R$_2$' that is longer than 'R$_1$'. Like the roughened portions described above with respect to FIG. 7A, each roughened portion illustrated in FIG. 713 is on an inner section of each of the flanks relative to a central axis of the implant (central axis not shown), and an outer section of each of the flanks (relative to the central axis) has roughness similar to the crests. The flattened crests 510b of FIG. 7B are similar to the crests 510a of FIG. 7A.

The threaded portion of FIG. 7C is similar to the threaded portion illustrated in FIGS. 7A and 7B, but includes narrower angled roots 520c instead of flattened or curved roots. Further, each of the flanks 530c has a length 'L$_3$', and a segment of each flank 530c has a roughened portion with a length 'R$_3$'. Like the roughened portions described above with respect to FIGS. 7A and 7B, each roughened portion illustrated in FIG. 7C is on an inner section of each of the flanks relative to a central axis of the implant (central axis not shown), and an outer section of each of the flanks (relative to the central axis) has roughness similar to the crests. The crests 510c of FIG. 7C are similar to the crests 510a of FIG. 7A and the crests 510h of FIG. 7B.

Figures 8A, 8B, 8C, 9:
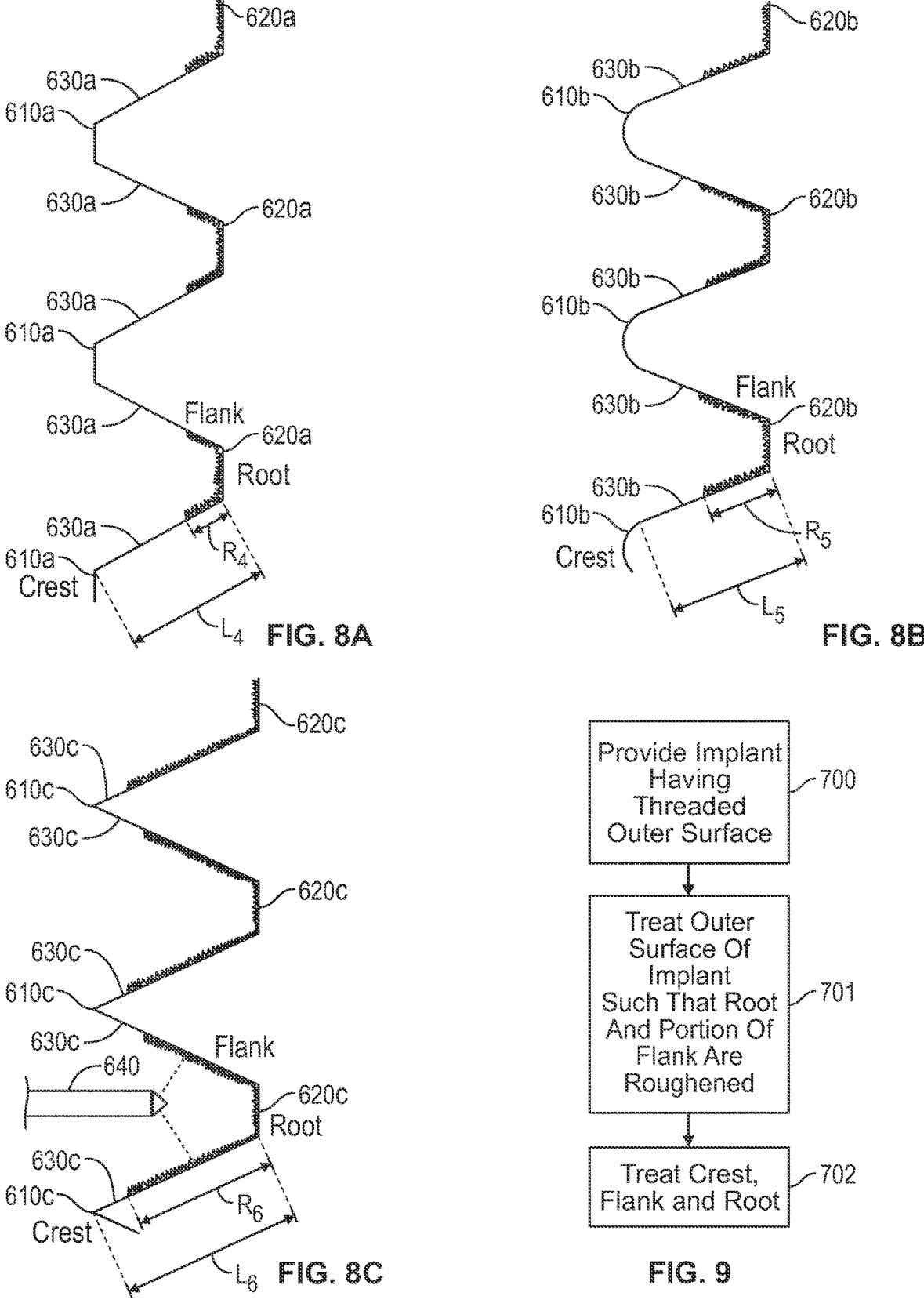
FIG. 8A illustrates a side view of the threaded portion of an implant with a flattened crest according to another aspect of the present invention.
FIG. 8B illustrates a side view of the threaded portion of an implant with a rounded crest according to another aspect of the present invention.
FIG. 8C illustrates a side view of the threaded portion of an implant with a peaked crest according to another aspect of the present invention.
FIG. 9 is a flow diagram illustrating a method of forming an implant according to an implementation of the present invention.

FIGS. 8A-8C illustrate side views of the threaded portion of implants with differently shaped crests according to the disclosed subject matter. Each of the threaded implant portions illustrated in FIGS. 8A-8C includes at least one root, flank, and crest. Like the threaded portion of FIG. 7A, the threaded portion of FIG. 8A includes crests 610a and roots 620a, each with a flattened shape, and multiple flanks 630a connecting the crests 610a and roots 620a. Each of the flanks 630a in the threaded portion of FIG. 8A has a length 'L$_4$', and a segment of each flank 630a has a roughened portion with a length 'R$_4$'. As shown in FIG. 8A, the roughened portion of the implant in FIG. 8A is on an inner section of each of the flanks 630a relative to a central axis of the implant (central axis not shown). Further, an outer section of each of the flanks 630a (relative to the central axis) has roughness similar to the crests 610a.

The threaded portion of FIG. 8B is similar to the threaded portion illustrated in FIG. 8A, but includes curved crests 610b instead of flattened crests. Further, each of the flanks 630h has a length 'L$_5$', and a segment of each flank 630b has a roughened portion with a length 'R$_5$'. Like the roughened portions described above with respect to FIG. 8A, each roughened portion illustrated in FIG. 8B is on an inner section of each of the flanks 630b relative to a central axis of the implant (central axis not shown), and an outer section of each of the flanks 630b (relative to the central axis) has roughness similar to the crests 610b. The roots 620b of FIG. 8B are similar to the roots 620a of FIG. 6A.

The threaded portion of FIG. 8C is similar to the threaded portion illustrated in FIGS. 8A and 8B, but includes peaked crests 610c instead of flattened or curved crests. Further, each of the flanks 630c has a length 'L$_6$', and a segment of each flank 630c has a roughened portion with a length 'R$_6$'. Like the roughened portions described above with respect to FIGS. 8A and 8B, each roughened portion illustrated in FIG. 8C is on an inner section of each of the flanks 630c relative to a central axis of the implant (central axis not shown), and an outer section of each of the flanks (relative to the central axis) has roughness similar to the crests 610c. The roots 620c of FIG. 8C are similar to the roots 620a of FIG. 8A and the roots 620b of FIG. 8B.

As shown in FIG. 8C, a nozzle 640 is placed between root and crest regions of the threaded portion. The nozzle 640 is used to perform grit blasting on the threaded portion and to appropriately roughen the threaded portion's surface. Optionally, the nozzle 640 can be guided by a laser or another optical or imaging device (not shown) that identifies the specific location of the nozzle 640 relative to the thread structure such that the blasting occurs between crest regions in a helical pattern along the root regions. For example, the laser or imaging device can identify and track the locations of the crests of two adjacent turns of the thread to ensure that the nozzle 640 remains substantially at the midpoint between those two adjacent crests. In an alternative implementation, a mask can be used to cover portions of the threaded portion in order to cover up areas that should not be treated or roughened.

As shown in FIGS. 7A-7C and 8A-8C, threaded implant portions as disclosed herein can have different shapes and sizes. More specifically, the flank regions connecting the root and the crest regions of the threaded portions can have different lengths and extend at different angles with respect to each other. Generally speaking the lengths of the flank regions range from 0.05 mm to 1 mm. In one preferred implementation, the length of the flank region is in the range from 0.1 mm to 0.3 mm. Further, in a preferred implementation, up to 95 percent of flank region can be roughened. In other implementations, the roughened portion makes up about 50% of the length of the flank region, in addition to the adjacent surface at the thread's root. In an implementation requiring less roughening, the roughened portion makes up about 25% of the length of the flank region, in addition to the adjacent surface at the thread's root. Other percentages of the flank region can roughened in other implementations.

Further, although not shown in FIGS. 7A-7C and 8A-8C, it is understood that the roughened portions of threads according to the disclosed subject matter can be asymmetrical That is, opposing flanks within a single turn of a thread can have roughened portions with different lengths. Additionally, the lengths of roughened portions within a thread can generally increase or decrease in a direction moving from the bottom of the thread towards the top of the thread. Portions of the implant that integrate with dense cortical bone can have increased roughness compared to portions of the implant that integrate with softer cancellous bone.

As would be understood by one of ordinary skill in the art, elements of the implementations in FIGS. 7A-7C and FIGS. 8A-8C may be combined with each other in accordance with the described subject matter. For example, different crest and root shapes as disclosed herein may be combined with each other as appropriate to form threads for implants as appropriate. Further, crest and root shapes other than those depicted in FIGS. 7A-7C and FIGS. 8A-8C may be incorporated in certain implementations of the disclosed subject matter. Similarly, flank shapes other than those depicted in FIGS. 7A-7C and FIGS. 8A-8C may be incorporated in other implementations of the disclosed subject matter. For example, certain implementations may incorporate convex flanks, concave flanks, wavelike flanks, or any other appropriate flank shape.

FIG. 9 is a flow diagram illustrating a method of forming an implant according to the disclosed subject matter. At step 700, an implant having a threaded outer surface is provided. Each thread includes at least one turn around the implant, and each turn has at least one root, one flank, and one crest. According to certain implementations, the implant is comprised of titanium, a titanium alloy, or the like. At step 701, the outer surface of the implant is treated such that only the root and a portion of the flank are roughened while the crest remains untreated. In certain implementations, the crest may be lightly treated compared to the root and the portion of the flank. For example, in certain implementations, the crest may be lightly acid etched while the root and the portion of the flank are more heavily acid etched. Optionally, only a portion of the length of the implant may be treated such that only some of the turns of the threads have roughened portions at their root regions. For example, according to certain implementations, only a fraction of the turns (e.g., one half of the turns) of the threaded outer surface may be treated along the lower portion of the implant, while the remainder of the threaded outer surface remains untreated.

Treating the outer surface at step 701 may include blasting the outer surface. The blasting can optionally be performed using a blast nozzle. When a blast nozzle is used to treat the outer surface, the blast nozzle can be inserted in between adjacent crests of the implant in order to treat only the desired region or regions. Further, in certain implementations, the blasting may be performed along a helical locus of the outer surface. According to certain implementations, other treatment methods may be used. For example, in certain implementations, the surface may be acid etched to create a roughened surface on the desired roots and/or flanks of the implant's outer surface.

The blast nozzle can blast different types of materials, and the different types of materials can have different particle sizes to produce different roughnesses on the outer surface of the implant. For example, in one implementation, calcium phosphate particles can be used as a blast material to treat the outer surface of an implant. The calcium phosphate particles can range in size, for example, from 150-425 microns. In addition to material types and particle sizes, other variables such as, for example, particle shape, particle hardness, particle flow rate, the size of the blast nozzle, the distance between the blast nozzle and the surface of the implant, the angle at which the nozzle is placed, and the type of gas used to accelerate the blasted materials can affect the roughness of the implant's outer surface.

After the outer surface is treated at step 701 the outer surface of the implant can undergo a second optional treatment at step 702. The further treatment can include treatment of the crest, flank and root regions with an acid etching treatment, which provides the outer surface of the implant with additional roughness. For example, in implementations where the implant is made of commercially pure titanium, a mixture including both hydrochloric acid and sulfuric acid may be used to perform acid etching, as described in U.S. Pat. No. 7,857,987, which is hereby incorporated by reference in its entirety. In implementations where the implant is made of titanium alloy, a mixture including both hydrochloric acid and hydrofluoric acid can be used to perform acid etching, as described in U.S. Pat. No. 8,251,700, which is hereby incorporated by reference in its entirety.

After a surface has been blasted at step 701 and acid etched at step 702, the entire threaded region has some roughness, with the crest regions remaining relatively smooth compared to the root regions and portions of the flank regions. For example, in certain implementations, the surface roughness, Ra, can be in the range of 0.7-1.6 microns along the root regions and flank regions that have been both grit-blasted and acid-etched, while the surface roughness, Ra, can be in the range of 0.3-0.7 microns along the crest regions that have been only acid-etched. In one particular implementation, the surface roughness, Ra, is about 1.3 microns along the root regions and flank regions that have been both grit blasted and acid etched, while the surface roughness, Ra, is about 0.5 microns along the crest regions that have been only acid etched. The surface roughness is preferably measured via the inverse Fourier transform (IFFT) method.

While particular implementations and applications of the present disclosure have been illustrated and described, it is to be understood that this disclosure is not limited to the precise construction and compositions disclosed herein and that various modifications, changes, and variations can be apparent from the foregoing descriptions without departing from the scope of the invention as defined in the appended claims.

What is claimed:

1. A dental implant for implantation into bone tissue having an exterior surface comprising:
  an elongated body extending from a first end to a second end and having an upper portion configured to receive a prosthesis, a lower portion for being submerged in the bone tissue, and an outer surface;
  at least one groove extending along at least a portion of the elongate body; and
  at least one thread on the outer surface making a plurality of turns around the elongated body between the lower portion and the upper portion, the at least one thread including a crest positioned between opposing roots and opposing flanks,
  wherein, throughout each of the plurality of turns, the opposing roots and an adjacent segment of each of the opposing flanks have a first roughened surface having a first roughness, the crest has a second roughened surface having a second roughness, and each of the flanks has a respective transition region including a portion of gradually decreasing roughness in a direction of the crest,
  a length of the first roughened surface and the respective transition region near the first end is different than the length of the first roughened surface and the respective transition region near the second end; and
  wherein the first roughness is greater than the second roughness.

2. The dental implant of claim 1, wherein the portion of the transition region transitions from the first roughness to the second roughness, wherein the elongated body has a center axis extending from the first end to the second end, and wherein the at least one groove extends parallel to the center axis and cuts the at least one thread.

3. The dental implant of claim 1, wherein the elongated body has a center axis extending from the first end to the second end, and wherein the at least one groove extends at an angle relative to the center axis.

4. The dental implant of claim 1, wherein the at least one groove extends along a length of the at least one thread.

5. The dental implant of claim 1, wherein the at least one groove has a third roughened surface having a third roughness.

6. The dental implant of claim 1, wherein the plurality of turns has a helical shape, wherein an inner section of each of the opposing flanks relative to a central axis of the dental implant has a roughened potion relative to the crest while an outer section of the flank relative to the central axis has a roughness similar to the crest and wherein the first roughness ranges from about 0.7 to about 1.6 microns.

7. The implant of claim 6, wherein the crest has one of a flattened shape, rounded shape and peaked shape, wherein each of the opposing roots has one of a flattened shape, a rounded shape, and an angled shape, and further comprising a self-tapping region positioned at a cutting tip in the lower portion of the elongated body, wherein the self-tapping region is radially offset from the at least one groove, wherein a distal end of the at least one groove is offset from the cutting tip, and wherein at least a portion of the at least one groove is positioned between the upper portion of the elongate body and the self-tapping region.

8. The dental implant of claim 1, wherein the first roughened surface is a first acid etched surface and the second roughened surface is a second acid etched surface.

9. The dental implant of claim 8, wherein the first acid etched surface bas a surface roughness of 0.7 to 1.6 microns and the second acid etched surface has a surface roughness of 0.3 to 0.7 microns.

10. The dental implant of claim 1, wherein each of the opposing roots has a rounded shape or wherein each of the opposing roots has an angled shape and wherein the second roughness of the crest ranges from about 0.3 to about 0.7 microns.

11. A dental implant for implantation into bone tissue, the dental implant having:
  at least one thread including a crest positioned between opposing roots and opposing flanks, the thread making a plurality of helical turns around the dental implant;
  wherein for each of the plurality of helical turns:
  a roughened portion is located adjacent to each of the opposing roots of the thread;
  the crest of the thread is relatively smooth; and
  a transition region is located on each of the opposing flanks of the at least one thread, the transition region including a portion of gradually decreasing roughness in a direction of the crest;
  a length of the roughened portion and the transition region near a first end of the dental implant is different than the length of the roughened portion and the transition region near a second end of the dental implant; and
  at least one groove extending along at least a portion of the at least one thread.

12. The dental implant of claim 11, wherein the dental implant has a center axis extending from the first end to the second end, and wherein the at least one groove extends parallel to the center axis and further comprising a self-tapping region positioned at a cutting tip of the at least one thread, wherein the self-tapping region is radially offset from the at least one groove, wherein a distal end of the at least one groove is offset from the cutting tip, and wherein at least a portion of the at least one groove is positioned between an upper end of the dental implant and the self-tapping region.

13. The dental implant of claim 11, wherein a roughness of the roughened portion ranges from about 0.7 to about 1.6 microns and wherein the crest has one of a flattened shape, rounded shape and peaked shape, and wherein each of the opposing roots has one of a flattened shape, a rounded shape, and an angled shape, wherein an elongated body of the implant has a center axis extending from the first end to the second end, and wherein the at least one groove extends at an angle relative to the center axis.

14. The dental implant of claim 11, wherein the plurality of turns has a helical shape, wherein an inner section of each of the opposing flanks relative to a central axis of the dental implant has a roughened potion relative to the crest while an outer section of each of the opposing flanks relative to the central axis has a roughness similar to the crest, wherein the portion of the transition region transitions from a first roughness to a second roughness, wherein the roughened portion adjacent to each of the opposing roots of the thread is a first roughened portion and the at least one groove has a second roughened portion.

15. A dental implant for implantation into bone tissue having an exterior surface comprising:

an elongated body extending from a first end to a second end and having an upper portion configured to receive a prosthesis, a lower portion for being submerged in the bone tissue, and an outer surface;

at least one groove extending along at least a portion of the elongate body; and at least one thread on the outer surface making a plurality of turns around the elongated body between the lower portion and the upper portion, the at least one thread including a root, a flank, and a crest, wherein around a circumference of each of the plurality of turns:

the root and a segment of the flank have a first roughened surface having a first roughness, the crest has a second roughened surface having a second roughness, and a transition region is positioned between the crest and the segment of the flank;

wherein a length of the first roughened surface and the transition region near the first end is different than the length of the first roughened surface and the transition region near the second end; and wherein the first roughness is greater than the second roughness, the transition region having a gradually decreasing roughness in a direction of the crest.

16. The dental implant of claim 15, further comprising a self-tapping region positioned at a cutting tip of the at least one thread in the lower portion of the elongated body;

wherein the self-tapping region is radially offset from the at least one groove;

wherein at least a portion of the at least one groove is positioned between the upper portion of the elongated body and the self-tapping region; and wherein a distal end of the at least one groove is offset from the cutting tip.

* * * * *